US012390585B2

(12) United States Patent
Dai

(10) Patent No.: US 12,390,585 B2
(45) Date of Patent: Aug. 19, 2025

(54) INFUSION SET FOR EFFORTLESS FLOW ADJUSTMENT

(71) Applicant: JIANGSU EBAY MEDICAL TECHNOLOGY CO., LTD., Suzhou (CN)

(72) Inventor: Xinchun Dai, Suzhou (CN)

(73) Assignee: JIANGSU EBAY MEDICAL TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 18/978,218

(22) Filed: Dec. 12, 2024

(65) Prior Publication Data

US 2025/0108161 A1   Apr. 3, 2025

Related U.S. Application Data

(63) Continuation of application No. PCT/CN2023/103604, filed on Jun. 29, 2023.

(30) Foreign Application Priority Data

Aug. 31, 2022 (CN) .......................... 202211051762.5

(51) Int. Cl.
*A61M 5/168* (2006.01)
*A61M 5/14* (2006.01)
*A61M 5/142* (2006.01)
*A61M 5/145* (2006.01)
*A61M 5/44* (2006.01)

(52) U.S. Cl.
CPC ...... *A61M 5/16804* (2013.01); *A61M 5/1413* (2013.01); *A61M 5/142* (2013.01); *A61M 5/16813* (2013.01); *A61M 5/44* (2013.01); *A61M 2005/14506* (2013.01); *A61M 2205/3334* (2013.01); *A61M 2205/366* (2013.01)

(58) Field of Classification Search
CPC .............. A61M 5/142; A61M 5/16813; A61M 2205/3334
See application file for complete search history.

(56) References Cited

FOREIGN PATENT DOCUMENTS

| CN | 112915313 A | 6/2021 |
|---|---|---|
| CN | 213667276 U | 7/2021 |
| CN | 215134649 U | 12/2021 |

(Continued)

*Primary Examiner* — Bradley J Osinski
(74) *Attorney, Agent, or Firm* — SZDC Law PC

(57) ABSTRACT

The invention provides an infusion set for effortless flow adjustment. The infusion set includes an installation base, a driving mechanism, and a connecting mechanism. The installation base has a cavity, and the driving mechanism and connecting mechanism are respectively installed on the installation base. The connecting beams are adeptly attached to the installation base through holes, while the connecting ring is affixed to these beams. Encasing the connecting beams, the first spring connects the installation base's cavity wall to the connecting ring, providing resilient support. The installation shaft, mounted on the movable base, hosts the pressure plate, facilitating pivotal movement. Simultaneously, the driving shaft, rotatably installed at the installation base's shaft hole, interfaces with the driving mechanism. The two ends of the second spring are respectively connected to the movable base and the pressure plate, and the driving shaft, integrated with the driving mechanism, governs the infusion set's operation.

9 Claims, 4 Drawing Sheets

(56) References Cited

FOREIGN PATENT DOCUMENTS

| | | |
|---|---|---|
| CN | 215608357 U | 1/2022 |
| CN | 114681712 A | 7/2022 |
| CN | 115382047 A | 11/2022 |
| JP | 2012161479 A | 8/2012 |

INFUSION SET FOR EFFORTLESS FLOW ADJUSTMENT

This application is a Continuation Application of PCT/CN2023/103604, filed on Jun. 29, 2023, which claims priority to Chinese Patent Application No. 202211051762.5, filed on Aug. 31, 2022, which is incorporated by reference for all purposes as if fully set forth herein.

FIELD OF THE INVENTION

The invention relates to the field of medical devices, more particularly to an infusion set for effortless flow adjustment.

DESCRIPTION OF THE RELATED ART

Infusion sets are essential medical consumables used to establish a channel between the vein and the medication for intravenous infusion. Typically, they consist of an intravenous needle or a needle, a needle cap, an infusion hose, a medication filter, a flow rate regulator, a drip pot, a cork trocar, and an air filter. Some infusion sets also have injection parts and dosing ports.

Currently, disposable infusion sets commonly employ a roller mechanism that rotates within an inclined cam groove to adjust the pressure on the infusion tubing, thereby regulating the flow rate. However, patients and their family members apply a large adjustment force when adjusting the infusion speed on their own, causing the roller to crawl and the adjustment amount to be discontinuous. Moreover, achieving precise adjustment of infusion speed proves challenging, resulting in either excessive or insufficient flow rates, thus diminishing the convenience and effectiveness of the adjustment process.

SUMMARY OF THE INVENTION

To solve the above-mentioned technical problems, the invention provides a novel infusion set that increases the diversity of functions, improves the convenience of operation, and increases the adaptability of use, making it effortless to adjust the flow rate.

The invention provides a novel infusion set for effortless flow adjustment, which comprises an installation base, a driving mechanism and a connecting mechanism, The installation base has a cavity. the driving and connecting mechanisms are installed on the installation base respectively. The driving mechanism is connected to the connecting mechanism. The connecting mechanism includes a movable base, connecting beams, a connecting ring, a first spring, an installation shaft, a pressure plate, a second spring, and a driving shaft. The two connecting beams are installed on the movable base, and the installation base is provided with two through holes, the connecting beams are slidably connected to the two through holes of the installation base, and the connecting ring is installed on the connecting beams. The first spring is sleeved outside the connecting beams, and the two ends of the first spring are respectively connected to the cavity wall of the installation base and the connecting ring. The installation shaft is rotatably mounted on the movable base, and the pressure plate is installed on the installation shaft, the installation shaft is provided with a polygon groove, and a shaft hole is provided on the installation base. The driving shaft is rotatably installed at the shaft hole of the installation base. The driving shaft is provided with a polygon column on one side thereof adjacent to the pressure plate, and the driving shaft is slidably connected to the installation base. The two ends of the second spring are respectively connected to the movable base and the pressure plate, and the driving shaft is connected to the driving mechanism.

For the novel infusion set for effortless flow adjustment of the invention, the driving mechanism includes a transmission worm gear, a support frame, a transmission worm, and linkage shafts. The transmission worm is coaxially installed on the driving shaft, the support frame is installed on the installation base, and a connection groove is provided on the support frame. The transmission worm gear is rotatably connected to the support frame by means of the connection groove. The transmission worm is engaged with the transmission worm gear in a transmission way, and the linkage shafts are coaxially installed on the transmission worm.

The novel infusion device for effortless flow adjustment includes a water storage tank positioned within the cavity of the installation base. Through holes are provided on the installation base, one side of the water storage tank is located at the through holes of the installation base, and an inlet and an outlet are respectively provided on the water storage tank. A connecting cover is provided at the inlet of the water storage tank, and a drainage valve is provided at the outlet of the water storage tank.

The novel infusion set for effortless flow adjustment of the invention further includes driving rods which are installed on two connecting beams respectively.

The novel infusion set for effortless flow adjustment of the invention further includes a driving wheel which is coaxially mounted on the linkage shaft.

The novel infusion set for effortless flow adjustment of the invention further includes a protective cover which is installed on the installation base, and the transmission worm gear and the transmission worm are both located inside the working chamber of the protective cover.

The novel infusion device for effortless flow adjustment further includes a connecting handle which is installed on the installation base.

The novel infusion set for effortless flow adjustment of the invention further includes a threaded rod. A threaded hole is provided on the movable base. The threaded rod is connected to the threaded hole of the movable base in coordination, and the pressure plate is in contact with the threaded rod.

For the novel infusion set for effortless flow adjustment of the invention, the installation base is equipped with a sealing cover, which is connected to the installation base through screws.

The novel infusion set for effortless flow adjustment of the invention further includes an adjustment wheel which is coaxially arranged on the threaded rod.

Compared with the prior art, the invention has the following advantages: two sets of connecting beams are used to make the movable base and the installation base in a sliding connection, effectively limiting the sliding trajectory. The connecting ring is used to connect the first spring with the connecting beams. The first spring is used to drive the connection positions between the movable base and the installation base, facilitating the provision of reset power after driving the connection position between the movable base and the installation base. It also facilitates reset power provision after driving the connection position, ensuring smooth operation, and preventing issues such as roller slippage or discontinuous adjustments. The polygon groove hole on the installation shaft is matched with the polygon column on the driving shaft to drive the pressure plate on the installation shaft to rotate. This rotational movement effectively regulates the flow rate by squeezing the infusion tube in conjunction with the installation base. The driving shaft is slidably connected to the installation shaft to drive the installation base and the movable base. This feature ensures precise control overflow rate adjustments and allows for easy detachment of the driving shaft from the installation shaft when moving away. The second spring plays a crucial role in separating the driving shaft from the installation shaft, facilitating reset power provision by the pressure plate. This mechanism ensures consistent and reliable performance during operation.

REFERENCE NUMERALS

1. Installation base; 2. movable base; 3. Connecting beams; 4. Connecting ring; 5. First spring; 6. Installation shaft; 7. Pressure plate; 8. Second spring; 9. Driving shaft; 10. Transmission worm gear; 11. Support frame; 12. Transmission worm; 13. Linkage shaft; 14. Water storage tank; 15. Driving rod; 16. Driving wheel; 17. Protective cover; 18. Connecting handle; 19. Threaded rod; 20. Sealing cover; 21. Adjustment wheel.

DETAILED DESCRIPTION OF THE PREFERRED EMBODIMENTS

The following is the detailed description of the invention in combination with the drawings and the embodiments. The embodiments provided herein serve to illustrate the invention's functionality and features but do not intend to restrict its scope.

Figure 1:
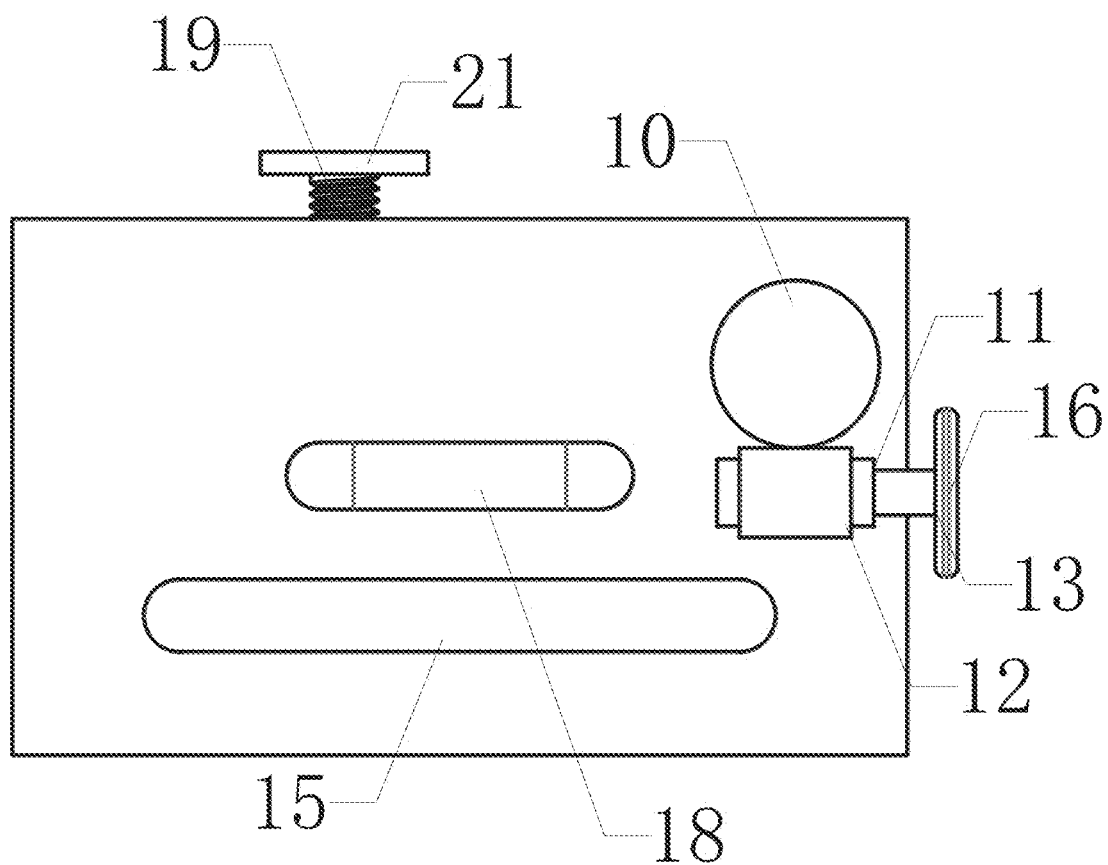
FIG. 1 is the orthographic structural diagram of the invention.
Figure 2:
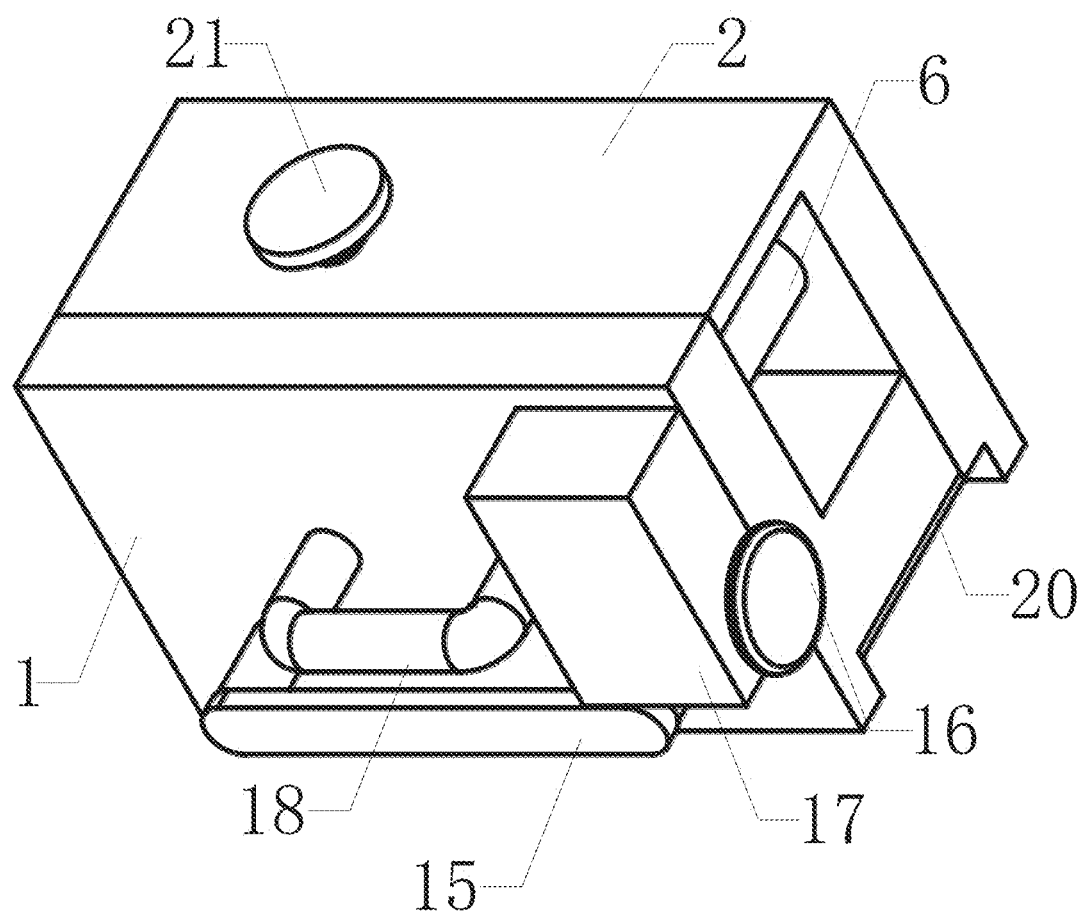
FIG. 2 is a schematic diagram of the axial side structure of the invention.
Figure 3:
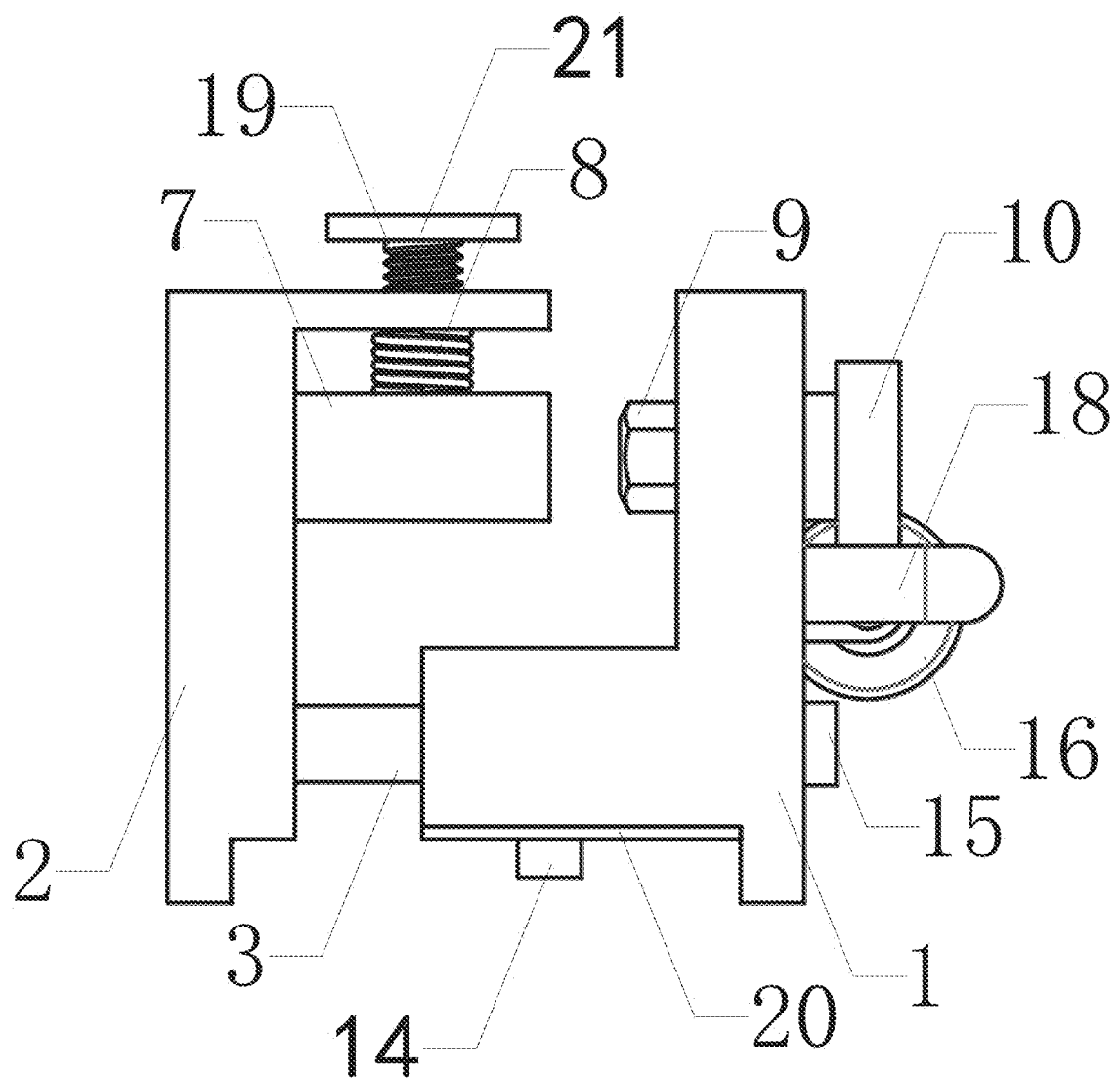
FIG. 3 is a schematic diagram of the working state of the invention.
Figure 4:
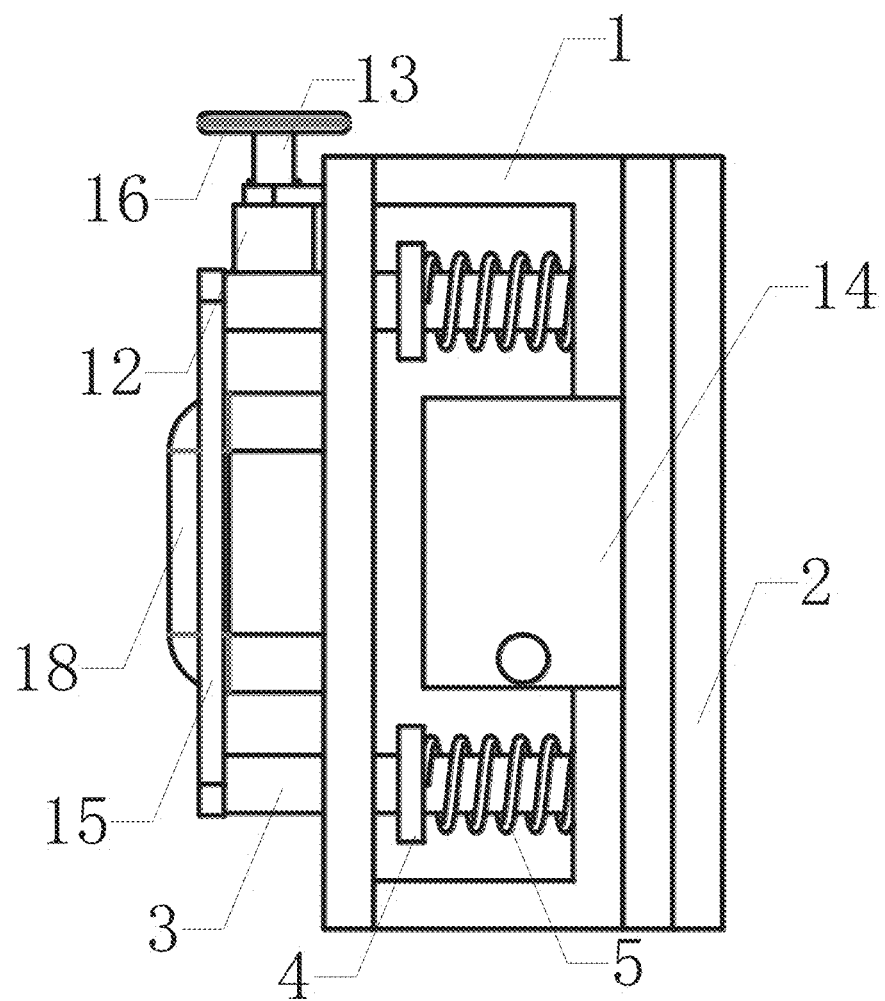
FIG. 4 is a schematic diagram of the top-down structure of the invention.

As shown in FIG. 1 to FIG. 4, the invention provides a novel infusion set for effortless flow adjustment, which comprises an installation base 1, a driving mechanism, and a connecting mechanism, wherein, the installation base 1 has a cavity, and the driving mechanism and the connecting mechanism are respectively installed on the installation base 1. The driving mechanism is connected to the connecting mechanism. The connecting mechanism comprises a movable base 2, connecting beams 3, a connecting ring 4, a first spring 5, an installation shaft 6, a pressure plate 7, a second spring 8 and a driving shaft 9. Two sets of connecting beams 3 are installed together on the movable base 2, and the installation base 1 is provided with two sets of through holes. The connecting beams 3 are slidably connected to the through holes of the installation base 1, and the connecting ring 4 is installed on the connecting beam 3. The first spring 5 is sleeved outside the connecting beam 3, and both ends of the first spring 5 are respectively connected to the cavity wall of the installation base 1 and the connecting ring 4. The installation shaft 6 is rotatably installed on the movable base 2, and the pressure plate 7 is installed on the installation shaft 6. The installation shaft 6 is provided with a polygon groove, and a shaft hole is provided on the installation base 1. The driving shaft 9 is rotatably installed at the shaft hole of the installation base 1. The driving shaft 9 is provided with a polygon column on one side thereof adjacent to the pressure plate 7, and the driving shaft 9 is slidably connected to the installation base 6. The two ends of the second spring 8 are respectively connected to the movable base 2 and the pressure plate 7, and the driving shaft 9 is connected to the driving mechanism. Two sets of connecting beams 3 are used to make the movable base 2 and the installation base 1 in a sliding connection, to limit the sliding trajectory. The connecting ring 4 is used to connect the first spring 5 with the connecting beam 3. The first spring 5 is used to drive the connection positions between the movable base 2 and the installation base 1, facilitating the provision of reset power after driving the connection position between the movable base 2 and the installation base 1, to drive the connecting beams 3 to separate the movable base 2 from the installation base 1, preventing the infusion tube from being inside the combination chamber of the installation base 1 and the movable base 2. The polygon groove on the installation shaft 6 are matched with the polygon column on the driving shaft 9 to drive the pressure plate 7 on the installation shaft 6 to rotate. The pressure plate 7 rotates and fits with the installation base 1 to squeeze the infusion tube and control the flow rate. The driving shaft 9 is slidably connected to the installation shaft 6 to drive the installation base 1 and the movable base 2. When moving away, the driving shaft 9 and installation shaft 6 are detached from each other. The second spring 8 separates the driving shaft 9 from the installation shaft 6, and then the pressure plate 7 provides reset power. The intention increases the diversity of functions, improves operational convenience, and increases usability.

In the novel infusion set for effortless flow adjustment of the invention, the adjustment mechanism comprises a transmission worm gear 10, a support frame 11, a transmission worm 12, and linkage shafts 13. The transmission worm 10 is coaxially installed on the driving shaft 9, the support frame 11 is installed on the installation base 1, and a connection groove is provided on the support frame 11. The transmission worm 12 is rotatably connected to the support frame 11 by means of the connection groove. The transmission worm 12 is engaged with the transmission worm 10 in a transmission way, and the linkage shafts 13 are coaxially installed on the transmission worm 12. The transmission worm 12 is rotatably supported on the installation base 1 through the support frame 11. The transmission worm 12 rotates to engage with the transmission worm gear 10, making the driving shaft 9 to provide rotational power to drive the pressure plate 7 on the installation shaft 6 to rotate, thereby controlling the flow rate of the infusion tube. The linkage shafts 13 increase the convenience of rotating the transmission worm 12. The engagement of the transmission worm 12 and the transmission worm gear 10 enables the device to have a self-locking function, improving device work stability and increasing device operation convenience.

The novel infusion device for effortless flow adjustment of the invention further comprises a water storage tank 14 which is installed inside the cavity of the installation base 1, and through holes are provided on the installation base 1. One side of the water storage tank 14 is located at the position of the through holes of the installation base 1, and an inlet and an outlet are respectively provided on the water storage tank 14. A connecting cover is provided at the inlet of the water storage tank 14, and a drainage valve is provided at the outlet of the water storage tank 14. The water inlet of water storage tank 14 is used to conveniently add hot water to the cavity of the water storage tank 14. The hot water in the cavity of the water storage tank 14 heats the infusion tube passing through the combination chamber of the installation base 1 and the movable base 2. This feature aims to alleviate potential discomfort for the patient caused by the low temperature of medication entering the body during wintry weather conditions. The drainage outlet of the water storage tank 14 is used to conveniently replace the water in the cavity, improving device use convenience, and increasing the diversity of device functions.

The novel infusion device for effortless flow adjustment of the invention further comprises driving rods 15 which are installed on two sets of connecting beams 3, respectively. The driving rods 15 are used to connect two sets of linkage shafts 13 in a coordinated manner to increase the driving difficulty of connecting beams 3, increase the contact area of the hand during the driving of connecting beams 3, enhancing driving comfort and providing added protection for the patients.

The novel infusion device for effortless flow adjustment of the invention further comprises a driving wheel 16 which is coaxially installed on the linkage shaft 13; The driving wheel 16 reduces the rotation difficulty of the linkage shaft 13, increases the rotation radius and transmission efficiency of the linkage shaft 13, and improves its adaptability for different usage scenarios.

The novel infusion device for effortless flow adjustment of the invention further comprises a protective cover 17 which is installed on the installation base 1, and the transmission worm gear 10 and transmission worm 12 are both located inside the working cavity of the protective cover 17. The protective cover 17 protects the transmission worm gear 10 and the transmission worm 12 during engaged transmission, effectively enhancing dust prevention measures within the device's transmission system. By doing so, it not only improves the operational safety of the device but also enhances its overall aesthetics.

The novel infusion device for effortless flow adjustment of the invention further comprises a connecting handle 18, which is installed on the installation base 1. The connecting handle 18 makes it effortless to access the installation base 1, increasing the convenience of operation at the positions for driving the movable base 2 and installation base 1, it further enhances the diversity of device functions and reduces the difficulty associated with operating the device, further improving the overall patients' experience.

The novel infusion device for effortless flow adjustment of the invention further comprises a threaded rod 19. There are threaded holes on the movable base 2. The threaded rod 19 is connected to the threaded hole on the movable base 2 in a matching manner, and the pressure plate 7 and the threaded rod 19 are in contact connection. The threaded rod 19 is connected to the threaded hole of the movable base 2. The driving shaft 9 rotates so that the connection location of the driving shaft 9 with the movable base 2 is adjusted synchronously, and the reset point of the pressure plate 7 is limited, to prevent the pressure plate 7 from repeating the process driven by wide-angle adjustment, thereby further improving the convenience in use of devices.

For the novel infusion device for effortless flow adjustment of the invention, the installation base 1 is provided with a sealing cover 20. The sealing cover 20 provides dust protection for the cavity of installation base 1. The sealing cover 20 is connected to the installation base 1 by screws, making it effortless to disassemble and improve the convenience of device assembly and maintenance, as well as the diversity of device functions.

The novel infusion device for effortless flow adjustment of the invention further comprises an adjustment wheel 21 which is coaxially arranged on the threaded rod 19. The adjustment wheel 21 reduces the difficulty of the rotation of the threaded rod 19, improves adjustment efficiency, and enhances device adaptability.

When using the novel infusion device for effortless flow adjustment of the invention, firstly, use four fingers other than the thumb to hold the connecting handle 18. Then, press the driving rods 15 with the thumb, and use the connecting beams 3 to drive the installation base 1 to move, causing the driving shaft 9 to detach from the installation shaft 6. Then, insert the infusion tube into the combination cavity through the opening of the separated installation base 1 and the movable base 2. Gradually release the driving rods 15 with the thumb, allowing the first spring 5's reset power to move the movable base 2 back into alignment with the installation base 1. As the movable base 2 realigns, ensure that the polygon groove hole of the installation shaft 6 connects with the polygon column of the driving shaft 9. Rotate the driving wheel 16, use the linkage shafts 13 to drive the transmission worm 12 to rotate, and rotate the transmission worm 12 to engage with the transmission worm gear 10 to drive the driving shaft 9 to rotate, and the driving shaft 9 cooperates with installation shaft 6 to drive pressure plate 7 to rotate. The pressure plate 7 cooperates with the installation base 1 to squeeze the infusion tube and control the flow rate. In cold weather conditions, warm water can be filled into the water storage tank 14 to heat the medication within the infusion tube. If the polygon groove hole of the installation shaft 6 fails to properly align and engage with the polygon column of the driving shaft 9, the driving wheel 16 can be rotated to adjust the position of the driving shaft 9 until a proper fit and engagement are achieved between the two components.

The novel infusion device for effortless flow adjustment of the invention can be installed, connected, or set up by conventional mechanical means. Any approach capable of achieving the desired beneficial effects can be employed The preceding embodiments represent preferred implementations of the invention. It's important to note that individuals skilled in the relevant technical field may devise improvements and variations that adhere to the underlying technical principles of the invention. Such enhancements and variations should also be considered within the scope of protection afforded by the invention.

What is claimed is:

1. An infusion set for effortless flow adjustment, comprising an installation base (1), a driving mechanism, and a connecting mechanism, wherein the installation base (1) has a cavity, the driving mechanism and the connecting mechanism are installed on the installation base (1) respectively, and the driving mechanism is connected to the connecting mechanism;

the connecting mechanism comprises a movable base (2), two connecting beams (3), a connecting ring (4), a first spring (5), an installation shaft (6), a pressure plate (7), a second spring (8), and a driving shaft (9), the two connecting beams (3) are installed on the movable base (2), and the installation base (1) is provided with two through holes, the two connecting beams (3) are slidably connected to the through holes of the installation base (1), and the connecting ring (4) is installed on the two connecting beams (3), the first spring (5) is sleeved outside the two connecting beams (3), and two ends of the first spring (5) are respectively connected to the cavity wall of the installation base (1) and the connecting ring (4), the installation shaft (6) is rotatably installed on the movable base (2), and the pressure plate (7) is installed on the installation shaft (6), the installation shaft (6) is provided with a polygon groove, and a shaft hole is provided on the installation base (1); the driving shaft (9) is rotatably installed at the shaft hole of the installation base (1), the driving shaft (9) is provided with a polygon column at one side thereof adjacent to the pressure plate (7), and the driving shaft (9) is slidably connected to the installation base (6), two ends of the second spring (8) are respectively connected to the movable base (2) and the pressure plate (7), and the driving shaft (9) is connected to the driving mechanism;

the driving mechanism comprises a transmission worm gear (10), a support frame (11), a transmission worm (12), and linkage shafts (13), the transmission worm gear (10) is coaxially installed on the driving shaft (9), the support frame (11) is installed on the installation base (1), and a connection groove is provided on the support frame (11), the transmission worm (12) is rotatably connected to the support frame (11) by means of the connection groove, the transmission worm (12) is engaged with the transmission worm gear (10) in a transmission way, and the linkage shafts (13) are coaxially installed on the transmission worm (12).

2. The infusion device for effortless flow adjustment according to claim 1, further comprising a water storage tank (14) which is mounted within the cavity of the installation base (1), one side of the water storage tank (14) is positioned at the through holes (1) of the installation base (1), and an inlet and an outlet are respectively provided on the water storage tank (14), a connecting cover is provided at the inlet of the water storage tank (14), and a drainage valve is provided at the outlet of the water storage tank (14).

3. The infusion set for effortless flow adjustment according to claim 1, further comprising driving rods (15) which are installed on the two connecting beams (3).

4. The infusion device for effortless flow adjustment according to claim 1, further comprising a driving wheel (16), which is coaxially mounted on the linkage shaft (13).

5. The infusion device for effortless flow adjustment according to claim 1, further comprising a protective cover (17) which is installed on the installation base (1), and the transmission worm gear (10) and the transmission worm (12) are both located inside a working chamber of the protective cover (17).

6. The infusion device for effortless flow adjustment according to claim 1, further comprising a connecting handle (18) which is installed on the installation base (1).

7. The infusion device for effortless flow adjustment according to claim 1, further comprising a threaded rod (19), a threaded hole is provided on the movable base (2), the threaded rod (19) is connected to the threaded hole of the movable base (2) in coordination, and the pressure plate (7) is in contact with the threaded rod (19).

8. The infusion set for effortless flow adjustment according to claim 1, wherein the installation base (1) is equipped with a sealing cover (20), which is connected to the installation base (1) through a screw.

9. The infusion device for effortless flow adjustment according to claim 7, further comprising an adjustment wheel (21) which is coaxially arranged on the threaded rod (19).

* * * * *